(12) United States Patent
Adam et al.

(10) Patent No.: US 9,233,886 B2
(45) Date of Patent: Jan. 12, 2016

(54) SIMULTANEOUS DEHYDRATION AND SKELETAL ISOMERISATION OF ISOBUTANOL ON ACID CATALYSTS

(75) Inventors: Cindy Adam, Wierde (BE); Delphine Minoux, Nivelles (BE); Nikolai Nesterenko, Nivelles (BE); Sander Van Donk, Guildford (GB); Jean-Pierre Dath, Beloeil (BE)

(73) Assignee: Total Research & Technology Feluy, Seneffe (Feluy) (BE)

( * ) Notice: Subject to any disclaimer, the term of this patent is extended or adjusted under 35 U.S.C. 154(b) by 97 days.

(21) Appl. No.: 13/582,759

(22) PCT Filed: Mar. 15, 2011

(86) PCT No.: PCT/EP2011/053902
§ 371 (c)(1),
(2), (4) Date: Oct. 8, 2012

(87) PCT Pub. No.: WO2011/113834
PCT Pub. Date: Sep. 22, 2011

(65) Prior Publication Data
US 2013/0204057 A1 Aug. 8, 2013

(30) Foreign Application Priority Data

Mar. 15, 2010 (EP) .................................. 10156537
Apr. 9, 2010 (EP) .................................. 10159463
Apr. 27, 2010 (EP) .................................. 10161125

(51) Int. Cl.
| | | |
|---|---|---|
| C07C 1/24 | (2006.01) | |
| B01J 29/85 | (2006.01) | |
| C07C 5/27 | (2006.01) | |
| C07C 11/08 | (2006.01) | |
| C07C 11/09 | (2006.01) | |
| C07C 5/25 | (2006.01) | |

(52) U.S. Cl.
CPC . *C07C 1/24* (2013.01); *B01J 29/85* (2013.01); *C07C 5/2518* (2013.01); *C07C 5/2775* (2013.01); *C07C 11/08* (2013.01); *C07C 11/09* (2013.01); *C07C 2529/70* (2013.01)

(58) Field of Classification Search
CPC .......... B01J 29/85; C07C 1/24; C07C 5/2775; C07C 11/08; C07C 11/09
See application file for complete search history.

(56) References Cited

U.S. PATENT DOCUMENTS

| | | | | |
|---|---|---|---|---|
| 6,768,035 | B2 * | 7/2004 | O'Rear et al. ................. | 585/331 |
| 6,977,318 | B2 | 12/2005 | Bridges | |
| 7,982,086 | B2 * | 7/2011 | Almering ....................... | 585/664 |
| 2007/0149839 | A1 * | 6/2007 | Rix et al. ....................... | 585/664 |
| 2008/0132741 | A1 | 6/2008 | D'Amore et al. | |
| 2008/0261230 | A1 | 10/2008 | Liao et al. | |

FOREIGN PATENT DOCUMENTS

| | | |
|---|---|---|
| DE | 890953 C | 10/1953 |
| EP | 2090561 A1 | 8/2009 |
| EP | 2108634 A1 | 10/2009 |
| WO | 9703932 A1 | 2/1997 |

OTHER PUBLICATIONS

Vendelin Macho, et al.; "Dehydration of C4 Alkanols Conjugated With a Positional and Skeletal Isomerisation of the Formed C4 Alkenes"; Applied Catalysis A: General, Elsevier Science, Amsterdam, N LNKD-, vol. 214, No. 2, pp. 251-257; Jun. 29, 2001; XP004241020; ISSN: 0926-860X.

(Continued)

*Primary Examiner* — In Suk Bullock
*Assistant Examiner* — Sharon Pregler

(57) ABSTRACT

The present invention (in a first embodiment) relates to a process for the simultaneous dehydration and skeletal isomerization of isobutanol to make substantially corresponding olefins, having the same number of carbons and consisting essentially of a mixture of n-butenes and isobutene, said process comprising:

a) introducing in a reactor a stream (A) comprising isobutanol, optionally water, optionally an inert component, b) contacting said stream with a catalyst in said reactor at conditions effective to dehydrate and skeletal isomerize at least a portion of the isobutanol to make a mixture of n-butenes and iso-butene, c) recovering from said reactor a stream (B), removing water, the inert component if any and unconverted isobutanol if any to get a mixture of n-butenes and iso-butene, Wherein, the WHSV of the isobutanol is at least 1 $h^{-1}$ or the temperature is from 200° C. to 600° C. and the catalyst is capable to make simultaneously the dehydration and skeletal isomerization of butene.

The catalyst is a crystalline silicate of the group FER, MWW, EUO, MFS, ZSM-48, MTT, MFI, MEL or TON having Si/Al higher than 10, or a dealuminated crystalline silicate of the group FER, MWW, EUO, MFS, ZSM-48, MTT, MFI, MEL or TON having Si/Al higher than 10, or a phosphorus modified crystalline silicate of the group FER, MWW, EUO, MFS, ZSM-48, MTT, MFI, MEL or TON having Si/Al higher than 10, or a silicoaluminaphosphate molecular sieve of the group AEL, or a silicated, zirconated or titanated or fluorinated alumina.

Advantageously the stream (B) is fractionated in a step d) to produce a n-butenes stream (N) and to remove the essential part of isobutene optionally recycled with stream (A) to the dehydration/isomerization reactor of step b).

28 Claims, 1 Drawing Sheet

(56) References Cited

OTHER PUBLICATIONS

John Warkentin, et al.; "Isobutane From Acid-Catalyzed Dehydration of Butanols"; Canadian Journal of Chemistry, vol. 48, pp. 3545-3548; Jan. 5, 1970; XP002595037.

V.M. Gyznevskii, et al.; "Oxidation of Isobutyl Alcohol on Fe-Te-Mo-O Catalyst"; Database CA [Online]; Chemical Abstracts Service, Columbus, Ohio, U.S.; & Kataliz l Neftekhimiya, vol. 12; pp. 74-77; 2003; XP002595038; Retrieved from STN Database accession No. 142:177154.

Kai A.N. Verkerk, et al.; "Recent Developments in Isobutanol Synthesis From Synthesis Gas"; Applied Catalysis A: General, vol. 186, pp. 407-431; 1999.

Carlo Carlini, et al.; "Selective Synthesis of Isobutanol by Means of the Guerbet Reaction Part 2. Reaction of Methanol/Ethanol and Methanol/Ethanol/n-Propanol Mixtures Over Copper Based/ MeONa Catalytic Systems"; Journal of Molecular Catalysis A: Chemical 200; pp. 137-146; 2003.

Ullmann's Encyclopedia of Industrial Chemistry, Sixth, Completely Revised Edition, vol. 5; 2002; pp. 721-722.

Von Helmut Bahrmann, et al.; "Fortschritte der Homologisierungsreaktion"; Chemiker-Zeitung, vol. 106, No. 6; Jahrgang; 1982; pp. 249-258.

Paul Meriaudeau, et al.; "Skeletal Isomerization of n-Butenes Catalyzed by Medium-Pore Zeolites and Aluminophosphates"; Advances in Catalysis, vol. 44; 2000; pp. 505-543.

Sander van Donk, et al.; "Deactivation of Solid Acid Catalysts for Butene Skeletal Isomerisation: On the Beneficial and Harmful Effects of Carbonaceous Deposits"; Applied Catalysis A: General, vol. 212; Elsevier; 2001; pp. 97-116.

J.H. De Boer, et al.; "Kinetics of the Dehydration of Alcohol on Alumina"; Journal of Catalysis, vol. 7; 1967; pp. 163-172.

Herman Pines, et al.; "Alumina: Catalyst and Support. IX. The Alumina Catalyzed Dehydration of Alcohols"; Journal of American Chemistry Soc., vol. 83; 1961, pp. 2847-2852.

Shota Atsumi, et al.; "Non-Fermentative Pathways for Synthesis of Branched-Chain Higher Alcohols as Biofuels"; Nature, Letters, vol. 451, p. 86-90; 2008.

"Catalytic Activity and Selectivity"; Stud. Surf. Sci, Catal., vol. 51, p. 260; 1989.

Edwin S. Olson, et al.; "Higher-Alcohols Biorefinery"; Applied Biochemistry and Biotechnology, vol. 113-116, pp. 913-932; 2004.

Peter A. Jacobs; "Carboniogenic Activity of Zeolites"; Elsevier Scientific Publishing Company, Amsterdam-Oxford-New York; p. 169; 1977.

M. Guisnet, et al.; "Selective Skeletal Butane Isomerization Through a Bimolecular Mechanism"; Oil & Gas Science and Technology, vol. 54, No. 1; 1999; pp. 23-28.

Office Action issued in Chinese Application No. 201180024174.6 dated Feb. 7, 2014, and an English translation thereof (14 pages).

* cited by examiner

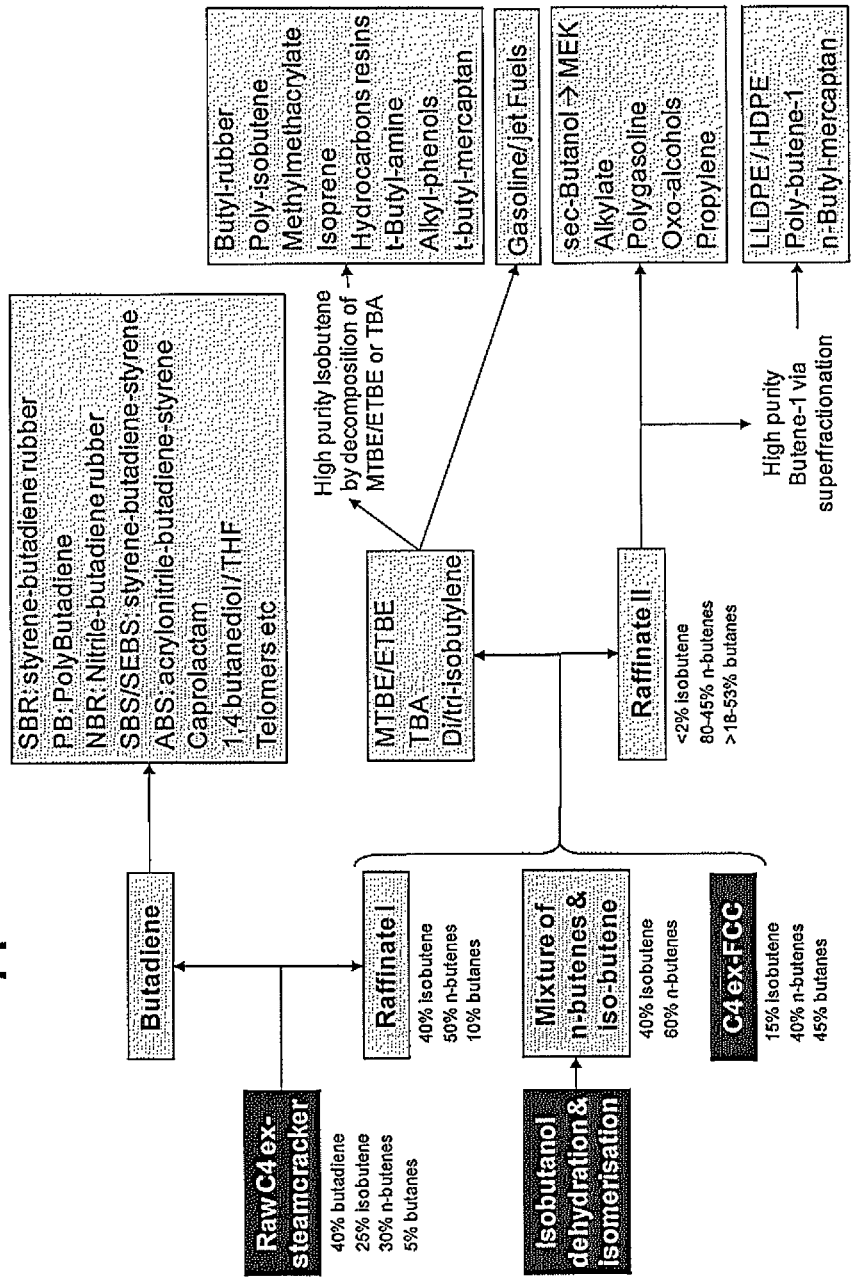

SIMULTANEOUS DEHYDRATION AND SKELETAL ISOMERISATION OF ISOBUTANOL ON ACID CATALYSTS

CROSS-REFERENCE TO RELATED APPLICATIONS

This application claims the benefit of PCT/EP2011/053902, filed Mar. 15, 2011, which claims priority from EP 10156537.2, filed Mar. 15, 2010, EP10159463.8, filed Apr. 9, 2010, and EP 10161125.9, filed Apr. 27, 2010.

FIELD OF THE INVENTION

The present invention relates to the simultaneous dehydration and skeletal isomerisation of isobutanol to make a corresponding olefin, having substantially the same number of carbons but different skeleton structure. The limited supply and increasing cost of crude oil has prompted the search for alternative processes for producing hydrocarbon products such as isobutene and n-butenes. Isobutanol can be obtained by fermentation of carbohydrates or by condensation of lighter alcohols, obtained by fermentation of carbohydrates. Made up of organic matter from living organisms, biomass is the world's leading renewable energy source.

BACKGROUND OF THE INVENTION

Isobutanol (2-methyl-1-propanol) has historically found limited applications and its use resembles that of 1-butanol. It has been used as solvent, diluents, wetting agent, cleaner additive and as additive for inks and polymers. Recently, isobutanol has gained interest as fuel or fuel component as it exhibits a high octane number (Blend Octane R+M/2 is 102-103) and a low vapor pressure (RVP is 3.8-5.2 psi).

Isobutanol is often considered as a byproduct of the industrial production of 1-butanol (Ullmann's encyclopedia of industrial chemistry, $6^{th}$ edition, 2002). It is produced from propylene via hydroformylation in the oxo-process (Rh-based catalyst) or via carbonylation in the Reppe-process (Co-based catalyst). Hydroformylation or carbonylation makes n-butanal and iso-butanal in ratios going from 92/8 to 75/25. To obtain isobutanol, the iso-butanal is hydrogenated over a metal catalyst. Isobutanol can also be produced from synthesis gas (mixture of CO, $H_2$ and $CO_2$) by a process similar to Fischer-Tropsch, resulting in a mixture of higher alcohols, although often a preferential formation of isobutanol occurs (Applied Catalysis A, general, 186, p. 407, 1999 and Chemiker Zeitung, 106, p. 249, 1982). Still another route to obtain isobutanol, is the base-catalysed Guerbet condensation of methanol with ethanol and/or propanol (J. of Molecular Catalysis A: Chemical 200, 137, 2003 and Applied Biochemistry and Biotechnology, 113-116, p. 913, 2004). Recently, new biochemical routes have been developed to produce selectively isobutanol from carbohydrates. The new strategy uses the highly active amino acid biosynthetic pathway of microorganisms and diverts its 2-keto acid intermediates for alcohol synthesis. 2-Keto acids are intermediates in amino acid biosynthesis pathways. These metabolites can be converted to aldehydes by 2-keto-acid decarboxylases (KDCs) and then to alcohols by alcohol dehydrogenases (ADHs). Two non-native steps are required to produce alcohols by shunting intermediates from amino acid biosynthesis pathways to alcohol production (Nature, 451, p. 86, 2008 and US patent 2008/0261230). Recombinant microorganisms are required to enhance the flux of carbon towards the synthesis of 2-keto-acids. In the valine biosynthesis 2-ketoisovalerate is on intermediate. Glycolyse of carbohydrates results in pyruvate that is converted into acetolactate by acetolactate synthase. 2,4-dihydroxyisovalerate is formed out of acetolactate, catalysed by isomeroreductase. A dehydratase converts the 2,4-dihydroxyisovalerate into 2-keto-isovalerate. In the next step, a keto acid decarboxylase makes isobutyraldehyde from 2-keto-isovalerate. The last step is the hydrogenation of isobutyraldehyde by a dehydrogenase into isobutanol.

Of the described routes towards isobutanol above, the Guerbet condensation, the synthesis gas hydrogenation and the 2-keto acid pathway from carbohydrates are routes that can use biomass as primary feedstock. Gasification of biomass results in synthesis gas that can be converted into methanol or directly into isobutanol. Ethanol is already at very large scale produced by fermentation of carbohydrates or via direct fermentation of synthesis gas into ethanol. So methanol and ethanol resourced from biomass can be further condensed to isobutanol. The direct 2-keto acid pathway can produce isobutanol from carbohydrates that are isolated from biomass. Simple carbohydrates can be obtained from plants like sugar cane, sugar beet. More complex carbohydrates can be obtained from plants like maize, wheat and other grain bearing plants. Even more complex carbohydrates can be isolated from substantially any biomass, through unlocking of cellulose and hemicellulose from lignocelluloses.

In the mid nineties, many petroleum companies attempted to produce more isobutene for the production of MTBE. Hence many skeletal isomerisation catalysts for the conversion of n-butenes into iso-butene have been developed (Adv. Catal. 44, p. 505, 1999; Oil & Gas Science and Technology, 54 (1) p. 23, 1999 and Applied Catalysis A: General 212, 97, 2001). Among promising catalysts are 10-membered ring zeolites and modified alumina's. The reverse skeletal isomerisation of iso-butene into n-butenes has not been mentioned.

The dehydration reactions of alcohols to produce alkenes have been known for a long time (J. Catal. 7, p. 163, 1967 and J. Am. Chem. Soc. 83, p. 2847, 1961). Many available solid acid catalysts can be used for alcohol dehydration (Stud. Surf. Sci. Catal. 51, p. 260, 1989). However, γ-aluminas are the most commonly used, especially for the longer chain alcohols (with more than three carbon atoms). This is because catalysts with stronger acidity, such as the silica-aluminas, molecular sieves, zeolites or resin catalysts can promote double-bond shift, skeletal isomerization and other olefin inter-conversion reactions. The primary product of the acid-catalysed dehydration of isobutanol is iso-butene:

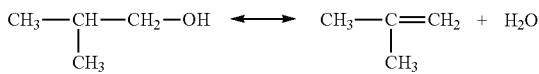

The dehydration of alcohols with four or more carbons over solid acid catalysts is expected to be accompanied by the double-bond shift reaction of the alkene product. This is because the two reactions occur readily and at comparable rates (Carboniogenic Activity of Zeolites, Elsevier Scientific Publishing Company, Amsterdam (1977) p. 169). The primary product, iso-butene is very reactive in presence of acid catalyst because of the presence of a double bond linked to a tertiary carbon. This allows easy protonation, as the tertiary structure of the resulting carbocation is the most favourable one among the possible carbocation structures (tertiary>secondary>primary carbocations). The resulting t-butyl-cation undergoes easy oligo/polymerisation or other electrophilic substitution on aromatics or aliphatics or electrophilic addition reactions. The rearrangement of t-butyl-cation is not a straightforward reaction as, without willing to be bound to any theory, involves an intermediate formation of secondary or primary butyl-cation and hence the probability of secondary reactions (substitutions or additions) is very high and would reduce the selectivity for the desired product.

Dehydration of butanols has been described on alumina-type catalysts (Applied Catalysis A, General, 214, p. 251, 2001). Both double-bond shift and skeletal isomerisation has been obtained at very low space velocity (or very long reaction time) corresponding to a GHSV (Gas Hourly Space Velocity=ratio of feed rate (gram/h) to weight of catalyst (ml)) of less than 1 gram·ml$^{-1}$·h$^{-1}$. The international patent application W02005/110951 describes a process for the production of propylene via metathesis of n-butenes that have been obtained via skeletal isomerisation of iso-butene which is produced from t-butanol via dehydration. All steps in the present application are carried out separately.

It has now been discovered that the dehydration and the skeletal isomerisation of the iso-butyl moiety in isobutanol can be carried out simultaneously.

By way of example it has been discovered that for the simultaneous dehydration and skeletal isomerisation of isobutanol, crystalline silicates of the group FER, MWW, EUO, MFS, ZSM-48, MTT or TON having Si/Al higher than 10, or a dealuminated crystalline silicate of the group FER, MWW, EUO, MFS, ZSM-48, MTT or TON having Si/Al higher than 10, or a phosphorus modified crystalline silicate of the group FER, MWW, EUO, MFS, ZSM-48, MTT or TON having Si/Al higher than 10, or molecular sieves of the type silicoaluminophosphate of the group AEL or silicated, zirconated or titanated alumina's or fluorinated alumina.

has many advantages. Said dehydration can be made with a WHSV (Weight Hourly Space Velocity=ratio of feed flow rate (gram/h) to catalyst weight) of at least 1 h$^{-1}$, at a temperature from 200 to 600° C. and using a isobutanol-diluent composition from 30 to 100% isobutanol at a total operating pressure from 0.05 to 1.0 MPa.

By way of example, in the dehydration/isomerisation of isobutanol on a ferrierite having a Si/Al ratio from 10 to 90 and with a WHSV of at least 2 h$^{-1}$ to make n-butenes beside iso-butene, the isobutanol conversion is at least 98% and often 99%, advantageously the butenes (iso and n-butenes) yield is at least 90%, the n-butenes selectivity is between 5% and the thermodynamic equilibrium at the given reaction conditions.

The isobutanol conversion is the ratio (isobutanol introduced in the reactor−isobutanol leaving the reactor)/(isobutanol introduced in the reactor).

The n-butenes yield is the ratio, on carbon basis, (n-butenes leaving the reactor)/(isobutanol introduced in the reactor).

The n-butenes selectivity is the ratio, on carbon basis, (n-butenes leaving the reactor)/(isobutanol converted in the reactor).

The simultaneous dehydration/isomerisation of isobutanol results in a mixture of n-butenes (but-1-ene and but-2-ene) and iso-butene. According to the present invention, often a composition close to thermodynamic equilibrium is obtained while maintaining the high yield of total butenes. The thermodynamic equilibrium for n-butenes varies between 50 and 65% and for iso-butene between 35 and 50% depending on operating conditions. An important advantage of the present invention is that the composition resembles the composition of a raffinate I C4 cut obtained from a steam naphtha cracker. Raffinate I is obtained by removing butadiene from the raw C4 cut produced on a steam naphtha cracker. Typical compositions are: 35-45% isobutene, 3-15% butanes and the remaining 52-40% n-butenes. It becomes evident that the product from the simultaneous dehydration/isomerisation can readily replace the use of raffinate I in existing petrochemical plants. The result is that capital investment can be minimised and that the derivatives from such iso-butene/n-butenes mixture can hence be produced from renewable resources instead of fossil resources simply by substituting fossil raffinate I by the product of the present invention.

EP 2090561 A1 describes the dehydration of an alcohol on crystalline silicates to get the corresponding olefin. Ethanol, propanol, butanol and phenylethanol are cited. Only ethanol is used in the examples. Nothing is cited about isobutanol and isomerisation thereof.

BRIEF SUMMARY OF THE INVENTION

The present invention (in a first embodiment) relates to a process for the simultaneous dehydration and skeletal isomerisation of isobutanol to make substantially corresponding olefins, having the same number of carbons and consisting essentially of a mixture of n-butenes and iso-butene, said process comprising:

a) introducing in a reactor a stream (A) comprising isobutanol, optionally water, optionally an inert component, b) contacting said stream with a catalyst in said reactor at conditions effective to dehydrate and skeletal isomerise at least a portion of the isobutanol to make a mixture of n-butenes and iso-butene, c) recovering from said reactor a stream (B), removing water, the inert component if any and unconverted isobutanol if any to get a mixture of n-butenes and iso-butene, Wherein, the WHSV of the isobutanol is at least 1 h$^{-1}$ and the catalyst is capable to make simultaneously the dehydration and skeletal isomerization of butene.

The present invention (in a second embodiment) relates to a process for the simultaneous dehydration and skeletal isomerisation of isobutanol to make substantially corresponding olefins, having the same number of carbons and consisting essentially of a mixture of n-butenes and iso-butene, said process comprising:

a) introducing in a reactor a stream (A) comprising isobutanol, optionally water, optionally an inert component, b) contacting said stream with a catalyst in said reactor at conditions effective to dehydrate and skeletal isomerise at least a portion of the isobutanol to make a mixture of n-butenes and iso-butene, c) recovering from said reactor a stream (B), removing water, the inert component if any and unconverted isobutanol if any to get a mixture of n-butenes and iso-butene, Wherein, the temperature ranges from 200° C. to 600° C. and the catalyst is capable to make simultaneously the dehydration and skeletal isomerization of butene.

The catalyst, in both embodiments, is a crystalline silicate of the group FER, MWW, EUO, MFS, ZSM-48, MTT, MFI, MEL or TON having Si/Al higher than 10, or a dealuminated crystalline silicate of the group FER, MWW, EUO, MFS, ZSM-48, MTT, MFI, MEL or TON having Si/Al higher than 10, or a phosphorus modified crystalline silicate of the group FER, MWW, EUO, MFS, ZSM-48, MTT, MFI, MEL or TON having Si/Al higher than 10, or a silicoaluminaphosphate molecular sieve of the group AEL, or a silicated, zirconated or titanated or fluorinated alumina.

A preferred catalyst, in both embodiments, is a crystalline silicate of the group FER or MFI having Si/Al higher than 10, or a dealuminated crystalline silicate of the group FER or MFI having Si/Al higher than 10, or a phosphorus modified crystalline silicate of the group FER or MFI having Si/Al higher than 10, In a specific embodiment the crystalline silicate of the group FER, MWW, EUO, MFS, ZSM-48, MTT, MFI, MEL or TON is steamed to remove aluminium from the crystalline silicate framework. The steam treatment is conducted at elevated temperature, preferably in the range of from 425 to 870° C., more preferably in the range of from 540 to 815° C. and at atmospheric pressure and at a water partial pressure of from 13 to 200 kPa. Preferably, the steam treatment is conducted in an atmosphere comprising from 5 to 100% steam. The steam atmosphere preferably contains from 5 to 100 vol % steam with from 0 to 95 vol % of an inert gas, preferably nitrogen. A more preferred atmosphere comprises 72 vol % steam and 28 vol % nitrogen i.e. 72 kPa steam at a pressure of one atmosphere. The steam treatment is preferably carried out for a period of from 0.1 to 200 hours, more preferably from 0.5 hour to 100 hours. As stated above, the steam treatment tends to reduce the amount of tetrahedral aluminium in the crystalline silicate framework as well as to enhance the resistance of the catalyst to regeneration.

In a more specific embodiment the crystalline silicate of the group FER, MWW, EUO, MFS, ZSM-48, MTT, MFI, MEL or TON is dealuminated by heating in steam to remove aluminium from the crystalline silicate framework and extracting aluminium from the catalyst by contacting the catalyst with an acid or a complexing agent for aluminium to remove from pores of the framework alumina deposited therein during the steaming step thereby to increase the silicon/aluminium atomic ratio of the catalyst. The catalyst having a high silicon/aluminium atomic ratio for use in the catalytic process of the present invention is manufactured by removing aluminium from a commercially available crystalline silicate. Accordingly, following the steaming step, the crystalline silicate is subjected to an extraction step wherein amorphous alumina is removed from the pores and the micropore volume is, at least partially, recovered. The physical removal, by a leaching step, of the amorphous alumina from the pores by the formation of a water-soluble aluminium complex yields the overall effect of de-alumination of the crystalline silicate. In this way by removing aluminium from the crystalline silicate framework and then removing alumina formed there from the pores, the process aims at achieving a substantially homogeneous de-alumination throughout the whole pore surfaces of the catalyst. This reduces the acidity of the catalyst. The reduction of acidity ideally occurs substantially homogeneously throughout the pores defined in the crystalline silicate framework. Following the steam treatment, the extraction process is performed in order to de-aluminate the catalyst by leaching. The aluminium is preferably extracted from the crystalline silicate by a complexing agent which tends to form a soluble complex with alumina. The complexing agent is preferably in an aqueous solution thereof. The complexing agent may comprise an organic or inorganic acid such as citric acid, formic acid, oxalic acid, tartaric acid, malonic acid, succinic acid, glutaric acid, adipic acid, maleic acid, phthalic acid, isophthalic acid, fumaric acid, nitrilotriacetic acid, hydroxyethylenediaminetriacetic acid, ethylenediaminetetracetic acid, trichloroacetic acid trifluoroacetic acid or a salt of such an acid (e.g. the sodium salt) or a mixture of two or more of such acids or salts. The acid agent may comprise an inorganic acid such as nitric acid, halogenic acids, sulphuric acid, phosphoric acid or salts of such acids or a mixture of such acids. The complexing agent may also comprise a mixture of such organic and inorganic acids or their corresponding salts. The complexing agent for aluminium preferably forms a water-soluble complex with aluminium, and in particular removes alumina which is formed during the steam treatment step from the crystalline silicate. A particularly preferred complexing agent may comprise an amine, preferably ethylene diamine tetraacetic acid (EDTA) or a salt thereof, in particular the sodium salt thereof.

Following the aluminium leaching step, the crystalline silicate may be subsequently washed, for example with distilled water, and then dried, preferably at an elevated temperature, for example around 110° C.

Additionally, if during the preparation of the catalysts of the invention alkaline or alkaline earth metals have been used, the molecular sieve might be subjected to an ion-exchange step. Conventionally, ion-exchange is done in aqueous solutions using ammonium salts or inorganic acids.

Following the de-alumination step, the catalyst is thereafter calcined, for example at a temperature of from 400 to 800° C. at atmospheric pressure for a period of from 1 to 10 hours.

It would not depart from the scope of the invention if the isobutanol feedstock comprises one or more of the other C4 alcohols such as 2-butanol, tertiobutanol and n-butanol. Advantageously isobutanol is the major component among alcohols in the feedstock, this means the ratio of isobutanol to all the C4 alcohols in the feedstock is 42% or above. More advantageously the previous ratio is 70% or more and preferably 80% or more. Of course if the proportion of isobutanol is too low the invention is of low interest, there are a lot of catalysts in the prior art capable to dehydrate 2-butanol and n-butanol to produce n-butenes.

In an advantageous embodiment the stream (B) is fractionated in a step d) to produce a n-butenes stream (N) and to remove the essential part of isobutene optionally recycled with stream (A) to the dehydration/isomerization reactor of step b). Recycling isobutene to the dehydration/isomerization reactor of step b) increases the n-butenes production.

In a specific embodiment in the fractionation of step d) iso-butene is removed by selective oligomerisation of iso-butene.

In a specific embodiment in the fractionation of step d) iso-butene is removed by selective etherification with methanol or ethanol.

In a specific embodiment in the fractionation of step d) iso-butene is removed by selective hydratation into t-butanol. Optionally said t-butanol is recycled to the dehydration/isomerization reactor of step b).

In a specific embodiment the fractionation of step d) is made by a catalytic distillation column wherein the essential part of 1-butene is isomerised to 2-butene, iso-butene is recovered as overhead and 2-butene is recovered in the bottoms of said column. Advantageously iso-butene is recycled to the dehydration/isomerization reactor of step b).

DETAILED DESCRIPTION OF THE INVENTION

As regards the stream (A), the isobutanol may be subjected to simultaneous dehydration and skeletal isomerisation alone or in mixture with an inert medium. The inert component is any component provided it is substantially not converted on the catalyst. Because the dehydration step is endothermic the inert component can be used as energy vector. The inert component allows reducing the partial pressure of the isobutanol and other reaction intermediates and will hence reduce secondary reactions like oligo/polymerisation. The inert component may be selected among water, nitrogen, hydrogen, CO2 and saturated hydrocarbons. It may be such that some inert components are already present in the isobutanol because they were used or co-produced during the production of isobutanol. Examples of inert components that may already be present in the isobutanol are water and CO2. The inert component may be selected among the saturated hydrocarbons having up to 10 carbon atoms, naphtenes. Advantageously it is a saturated hydrocarbon or a mixture of saturated hydrocarbons having from 3 to 7 carbon atoms, more advantageously having from 4 to 6 carbon atoms and is preferably pentane. An example of inert component can be any individual saturated compound, a synthetic mixture of the individual saturated compounds as well as some equilibrated refinery streams like straight naphtha, butanes etc. Advantageously the inert component is a saturated hydrocarbon having from 3 to 6 carbon atoms and is preferably pentane. The weight proportions of respectively isobutanol and inert component are, for example, 30-100/70-0 (the total being 100). The stream (A) can be liquid or gaseous.

As regards the reactor, it can be a fixed bed reactor, a moving bed reactor or a fluidized bed reactor. A typical fluid bed reactor is one of the FCC type used for fluidized-bed catalytic cracking in the oil refinery. A typical moving bed reactor is of the continuous catalytic reforming type. The simultaneous dehydration/isomerisation may be performed continuously in a fixed bed reactor configuration using a pair of parallel "swing" reactors. The various preferred catalysts of the present invention have been found to exhibit high stability. This enables the dehydration process to be performed continuously in two parallel "swing" reactors wherein when one reactor is operating, the other reactor is undergoing catalyst regeneration. The catalyst of the present invention also can be regenerated several times.

The simultaneous dehydration/isomerisation may be performed continuously in a moving bed reactor in which the catalyst circulates from a reaction zone to a regeneration zone and backwards with a residence time of the catalyst in the reaction zone of at least 12 hours. In each zone the catalyst behaves substantially like in a fixed bed reactor, but the catalyst moves slowly, by gravity or pneumatically through the respective zone. The use of a moving bed reaction allows accomplishing a continuous operation with no switching of the feedstock and regeneration gas from one reactor to another one. The reaction zone receives continuously the feedstock while the regeneration zone receives continuously the regeneration gas.

The simultaneous dehydration/isomerisation may be performed continuously in a fluidised bed reactor in which the catalyst circulates from a reaction zone to a regeneration zone and backwards with a residence time of the catalyst in the reaction zone of less than 12 hours. In each zone the catalyst is in a fluidised state and exhibit such a shape and size that it remains fluidised in the flow of the feedstock and reaction products or regeneration gas. The use of a fluidised bed reactor allows regenerating very rapidly deactivated catalyst by regeneration in the regeneration zone.

As regards the pressure, it can be any pressure but it is more easy and economical to operate at moderate pressure. By way of example the pressure of the reactor ranges from 0.5 to 10 bars absolute (50 kPa to 1 MPa), advantageously from 0.5 to 5 bars absolute (50 kPa to 0.5 MPa), more advantageously from 1.2 to 5 bars absolute (0.12 MPa to 0.5 MPa) and preferably from 1.2 to 4 bars absolute (0.12 MPa to 0.4 MPa). Advantageously the partial pressure of the isobutanol is from 0.1 to 4 bars absolute (0.01 MPa to 0.4 MPa), more advantageously from 0.5 to 3.5 bars absolute (0.05 MPa to 0.35 MPa).

As regards the temperature, and the first embodiment it ranges from 200° C. to 600° C., advantageously from 250° C. to 500° C., more advantageously from 300° C. to 450° C. As regards the temperature and the second embodiment it ranges from 200° C. to 600° C., advantageously from 250° C. to 500° C., more advantageously from 300° C. to 450° C.

These reaction temperatures refer substantially to average catalyst bed temperature. The isobutanol dehydration is an endothermic reaction and requires the input of reaction heat in order to maintain catalyst activity sufficiently high and shift the dehydration thermodynamic equilibrium to sufficiently high conversion levels.

In case of fluidised bed reactors: (i) for stationary fluidised beds without catalyst circulation, the reaction temperature is substantially homogeneous throughout the catalyst bed; (ii) in case of circulating fluidised beds where catalyst circulates between a converting reaction section and a catalyst regeneration section, depending on the degree of catalyst backmixing the temperature in the catalyst bed approaches homogeneous conditions (a lot of backmixing) or approaches plug flow conditions (nearly no backmixing) and hence a decreasing temperature profile will install as the conversion proceeds.

In case of fixed bed or moving bed reactors, a decreasing temperature profile will install as the conversion of the isobutanol proceeds. In order to compensate for temperature drop and consequently decreasing catalyst activity or approach to thermodynamic equilibrium, reaction heat can be introduced by using several catalyst beds in series with interheating of the reactor effluent from the first bed to higher temperatures and introducing the heated effluent in a second catalyst bed, etc. When fixed bed reactors are used, a multi-tubular reactor can be used where the catalyst is loaded in small-diameter tubes that are installed in a reactor shell. At the shell side, a heating medium is introduced that provides the required reaction heat by heat-transfer through the wall of the reactor tubes to the catalyst.

As regards the WHSV of the isobutanol, and the first embodiment it ranges advantageously from 1 to 30 $h^{-1}$, preferably from 2 to 21 $h^{-1}$, more preferably from 7 to 12 $h^{-1}$. As regards the second embodiment it ranges advantageously from 1 to 30 $h^{-1}$, more advantageously from 2 to 21 $h^{-1}$, preferably from 5 to 15 $h^{-1}$, more preferably from 7 to 12 $h^{-1}$.

As regards the stream (B), it comprises essentially water, olefin, the inert component (if any) and unconverted isobutanol. Said unconverted isobutanol is supposed to be as less as possible. The olefin is recovered by usual fractionation means. Advantageously the inert component, if any, is recycled in the stream (A) as well as the unconverted isobutanol, if any. Unconverted isobutanol, if any, is recycled to the reactor in the stream (A).

Advantageously among the butenes the proportion of n-butenes is above 20%, advantageously above 30%, more advantageously above 40%, preferably above 50%.

As regards the catalyst, it is a crystalline silicate of the group FER (ferrierite, FU-9, ZSM-35), MWW (MCM-22, PSH-3, ITQ-1, MCM-49), EUO (ZSM-50, EU-1), MFS (ZSM-57), ZSM-48, MTT (ZSM-23), MFI (ZSM-5), MEL (ZSM-11) or TON (ZSM-22, Theta-1, NU-10), or a dealuminated crystalline silicate of the group FER (ferrierite, FU-9, ZSM-35), MWW (MCM-22, PSH-3, ITQ-1, MCM-49), EUO (ZSM-50, EU-1), MFS (ZSM-57), ZSM-48, MTT (ZSM-23), MFI (ZSM-5), MEL (ZSM-11) or TON (ZSM-22, Theta-1, NU-10), or a phosphorus modified crystalline silicate of the group FER (ferrierite, FU-9, ZSM-35), MWW (MCM-22, PSH-3, ITQ-1, MCM-49), EUO (ZSM-50, EU-1), MFS (ZSM-57), ZSM-48, MTT (ZSM-23), MFI (ZSM-5), MEL (ZSM-11) or TON (ZSM-22, Theta-1, NU-10), or a silicoaluminophosphate molecular sieve of the group AEL (SAPO-11), or a silicated, zirconated or titanated or fluorinated alumina.

About the crystalline silicate of FER structure (ferrierite, FU-9, ZSM-35) it can be the lamellar precursor which becomes FER by calcinations.

The Si/Al ratio is advantageously higher than 10.

The crystalline silicate is such as the Si/Al ratio ranges more advantageously from 10 to 500, preferably from 12 to 250, more preferably from 15 to 150.

The acidity of the catalyst can be determined by the amount of residual ammonia on the catalyst following contact of the catalyst with ammonia which adsorbs on the acid sites of the catalyst with subsequent ammonium desorption at elevated temperature measured by differential thermogravimetric analysis or analysis of ammonia concentration in the desorbed gases.

The crystalline silicate can be subjected to various treatments before use in the dehydration including, ion exchange, modification with metals (in a not restrictive manner alkali, alkali-earth, transition, or rare earth elements), external surface passivation, modification with P-compounds, steaming, acid treatment or other dealumination methods, or combination thereof.

In a specific embodiment the crystalline silicate is steamed to remove aluminium from the crystalline silicate framework. The steam treatment is conducted at elevated temperature, preferably in the range of from 425 to 870° C., more preferably in the range of from 540 to 815° C. and at atmospheric pressure and at a water partial pressure of from 13 to 200 kPa. Preferably, the steam treatment is conducted in an atmosphere comprising from 5 to 100 vol % steam. The steam atmosphere preferably contains from 5 to 100 vol % steam with from 0 to 95 vol % of an inert gas, preferably nitrogen. The steam treatment is preferably carried out for a period of from 1 to 200 hours, more preferably from 4 hours to 10 hours. As stated above, the steam treatment tends to reduce the amount of tetrahedral aluminium in the crystalline silicate framework, by forming alumina.

In a more specific embodiment the crystalline silicate is dealuminated by heating the catalyst in steam to remove aluminium from the crystalline silicate framework and extracting aluminium from the catalyst by contacting the catalyst with a complexing agent for aluminium to remove from pores of the framework alumina deposited therein during the steaming step thereby to increase the silicon/aluminium atomic ratio of the catalyst. In accordance with the present invention, the commercially available crystalline silicate is modified by a steaming process which reduces the tetrahedral aluminium in the crystalline silicate framework and converts the aluminium atoms into octahedral aluminium in the form of amorphous alumina. Although in the steaming step aluminium atoms are chemically removed from the crystalline silicate framework structure to form alumina particles, those particles cause partial obstruction of the pores or channels in the framework. This could inhibit the dehydration process of the present invention. Accordingly, following the steaming step, the crystalline silicate is subjected to an extraction step wherein amorphous alumina is removed from the pores and the micropore volume is, at least partially, recovered. The physical removal, by a leaching step, of the amorphous alumina from the pores by the formation of a water-soluble aluminium complex yields the overall effect of de-alumination of the crystalline silicate. In this way by removing aluminium from the crystalline silicate framework and then removing alumina formed therefrom from the pores, the process aims at achieving a substantially homogeneous de-alumination throughout the whole pore surfaces of the catalyst. This reduces the acidity of the catalyst. The reduction of acidity ideally occurs substantially homogeneously throughout the pores defined in the crystalline silicate framework. Following the steam treatment, the extraction process is performed in order to de-aluminate the catalyst by leaching. The aluminium is preferably extracted from the crystalline silicate by a complexing agent which tends to form a soluble complex with alumina. The complexing agent is preferably in an aqueous solution thereof. The complexing agent may comprise an organic acid such as citric acid, formic acid, oxalic acid, tartaric acid, malonic acid, succinic acid, glutaric acid, adipic acid, maleic acid, phthalic acid, isophthalic acid, fumaric acid, nitrilotriacetic acid, hydroxyethylenediaminetriacetic acid, ethylenediaminetetracetic acid, trichloroacetic acid trifluoroacetic acid or a salt of such an acid (e.g. the sodium salt) or a mixture of two or more of such acids or salts. The complexing agent may comprise an inorganic acid such as nitric acid, halogenic acids, sulphuric acid, phosphoric acid or salts of such acids or a mixture of such acids. The complexing agent may also comprise a mixture of such organic and inorganic acids or their corresponding salts. The complexing agent for aluminium preferably forms a water-soluble complex with aluminium, and in particular removes alumina which is formed during the steam treatment step from the crystalline silicate.

Following the aluminium leaching step, the crystalline silicate may be subsequently washed, for example with distilled water, and then dried, preferably at an elevated temperature, for example around 110° C.

Additionally, if during the preparation of the catalysts of the invention alkaline or alkaline earth metals have been used, the molecular sieve might be subjected to an ion-exchange step. Conventionally, ion-exchange is done in aqueous solutions using ammonium salts or inorganic acids.

Following the de-alumination step, the catalyst is thereafter calcined, for example at a temperature of from 400 to 800° C. at atmospheric pressure for a period of from 1 to 10 hours.

Another suitable catalyst for the present process is the silicoaluminophosphate molecular sieves of the AEL group with typical example the SAPO-11 molecular sieve. The SAPO-11 molecular sieve is based on the ALPO-11, having essentially an Al/P ratio of 1 atom/atom. During the synthesis silicon precursor is added and insertion of silicon in the ALPO framework results in an acid site at the surface of the micropores of the 10-membered ring sieve. The silicon content ranges from 0.1 to 10 atom % (Al+P+Si is 100).

In another specific embodiment the crystalline silicate or silicoaluminophosphate molecular sieve is mixed with a binder, preferably an inorganic binder, and shaped to a desired shape, e.g. pellets. The binder is selected so as to be resistant to the temperature and other conditions employed in the dehydration process of the invention. The binder is an inorganic material selected from clays, silica, metal silicates, metal oxides such as $ZrO_2$ and/or metals, or gels including mixtures of silica and metal oxides. If the binder which is used in conjunction with the crystalline silicate is itself catalytically active, this may alter the conversion and/or the selectivity of the catalyst. Inactive materials for the binder may suitably serve as diluents to control the amount of conversion so that products can be obtained economically and orderly without employing other means for controlling the reaction rate. It is desirable to provide a catalyst having a good crush strength. This is because in commercial use, it is desirable to prevent the catalyst from breaking down into powder-like materials. Such clay or oxide binders have been employed normally only for the purpose of improving the crush strength of the catalyst. A particularly preferred binder for the catalyst of the present invention comprises silica. The relative proportions of the finely divided crystalline silicate material and the inorganic oxide matrix of the binder can vary widely. Typically, the binder content ranges from 5 to 95% by weight, more typically from 20 to 75% by weight, based on the weight of the composite catalyst. Such a mixture of the crystalline silicate and an inorganic oxide binder is referred to as a formulated crystalline silicate. In mixing the catalyst with a binder, the catalyst may be formulated into pellets, extruded into other shapes, or formed into spheres or a spray-dried powder. Typically, the binder and the crystalline silicate are mixed together by a mixing process. In such a process, the binder, for example silica, in the form of a gel is mixed with the crystalline silicate material and the resultant mixture is extruded into the desired shape, for example cylindrical or multi-lobe bars. Spherical shapes can be made in rotating granulators or by oil-drop technique. Small spheres can further be made by spray-drying a catalyst-binder suspension. Thereafter, the formulated crystalline silicate is calcined in air or an inert gas, typically at a temperature of from 200 to 900° C. for a period of from 1 to 48 hours.

In addition, the mixing of the catalyst with the binder may be carried out either before or after the steaming and extraction steps.

Another family of suitable catalysts for the simultaneous dehydration and skeletal isomerisation are alumina's that have been modified by surface treatment with silicon, zirconium or titanium. Alumina's are generally characterised by a rather broad acid strength distribution and having both Lewis-type and Bronsted-type acid sites. The presence of a broad acid strength distribution makes the catalysis of several reactions, requiring each a different acid strength, possible. This often results in low selectivity for the desired product. Deposition of silicon, zirconium or titanium on the surface of alumina allows rendering the catalyst significantly more selective. For the preparation of the alumina based catalyst, suitable commercial alumina's can be used, preferably eta or gamma alumina, having a surface area of 10 to 500 m2/gram and an alkali content of less than 0.5%. The catalyst according to the present invention is prepared by adding 0.05 to 10% of silicon, zirconium or titanium. The addition of these metals can be done during the preparation of the alumina or can be added to the existing alumina, eventually already activated. Addition of the metal during the preparation of the alumina can be done by dissolving the metal precursor together with the aluminium precursor before precipitation of the final alumina or by addition of the metal precursor to the aluminium hydroxide gel. A preferred method is adding metal precursors to the shaped alumina. Metal precursors are dissolved in a suitable solvent, either aqueous or organic, and contacted with the alumina by incipient wetness impregnation or by wet impregnation or by contacting with an excess of solute during a given time, followed by removing the excess solute. The alumina can also be contacted with vapour of the metal precursor. Suitable metal precursors are halides of silicon, zirconium or titanium, oxyhalides of zirconium or titanium; alcoxides of silicon, zirconium or titanium; oxalates or citrates of zirconium or titanium or mixtures of the above. The solvent is selected according to the solubility of the metal precursor. The contacting can be done at temperature of 0° C. to 500° C., most preferred from 10° C. to 200° C. After the contacting, the alumina is eventually washed, dried and finally calcined in other to enhance the surface reaction between the silicon, zirconium or titanium and the alumina and the removal of the metal precursor ligands. The use of silicated, zirconated or titanated or fluorinated alumina's for the simultaneous dehydration and skeletal isomerisation of isobutanol is preferably done in the presence of water. The weight ratio of water to isobutanol ranges from 1/25 to 3/1. Fluorinated alumina is known in itself and can be made according to the prior art.

As regards the use of the product, the mixture of n-butenes and iso-butene can replace the use of raffinate I in the refinery or petrochemical plants. FIG. 1 shows the main applications of n-butenes and isobutene. The most typical application of such mixture is the conversion of the contained iso-butene into ethers (MTBE and ETBE), into t-butylalcohol (TBA) or oligomers (e.g. di/tri-iso-butenes), all being gasoline components. The higher oligomers of iso-butene can be used for jet fuel applications. High purity iso-butene can further be made by the decomposition of ethers (backcracking) or TBA (dehydration). High purity iso-butene finds applications in the production of Butyl-rubber, Poly-isobutene, Methylmethacrylate, Isoprene, Hydrocarbons resins, t-Butyl-amine, Alkyl-phenols and t-butyl-mercaptan.

The n-butenes, having not reacted during the production of ethers or TBA and substantially not or only to a limited extend during the oligomerisation, have applications in the production of sec-Butanol, Alkylate (addition of isobutane to butenes), Polygasoline, Oxo-alcohols and Propylene (metathesis with ethylene or self-metathesis between but-1-ene and but-2-ene). By means of superfractionation or extractive distillation or absorptive separation but-1-ene can be isolated from the n-butenes mixture. But-1-ene is used as comonomer for the production of polyethylenes, for poly-but-1-ene and n-butyl-mercaptan.

n-Butenes can also be separated from iso-butene by means of a catalytic distillation. This involves an isomerisation catalyst that is located in the distillation column and continuously converts the but-1-ene into but-2-ene, being a heavier component than but-1-ene. Doing so, a bottom product rich in but-2-ene and a top product poor in but-1-ene and rich in iso-butene is produced. The bottom product can be used as described above. One main application of such but-2-ene rich stream is the metathesis with ethylene in order to produce propylene. If high purity iso-butene is desired the top product can be further superfractionated into substantially pure iso-butene and pure but-1-ene or the iso-butene can be isolated via formation of ethers or TBA that is subsequently decomposed into pure iso-butene.

The n-butenes rich stream may be used for the production of butadiene via dehydrogenation or oxidative dehydrogenation.

The mixture of isobutene and butenes can be sent to a catalytic cracking which is selective towards light olefins in the effluent, the process comprising contacting said isobutene and butenes mixture with an appropriate catalyst to produce an effluent with an olefin content of lower molecular weight than that of the feedstock. Said cracking catalyst can be a silicalite (MFI or MEL type) or a P-ZSM5.

EXAMPLES

Experimental

The stainless-steel reactor tube has an internal diameter of 10 mm. 10 ml of catalyst, as pellets of 35-45 mesh, is loaded in the tubular reactor. The void spaces before and after the catalyst are filled with SiC granulates of 2 mm. The temperature profile is monitored with the aid of a thermocouple well placed inside the reactor. The reactor temperature is increased at a rate of 60° C./h to 550° C. under air, kept 2 hours at 550° C. and then purged by nitrogen. The nitrogen is then replaced by the feed at the indicated operating conditions.

The catalytic tests are performed down-flow, at 1.5 and 2.0 bara, in a temperature range of 280-380° C. and with a weight hour space velocity (WHSV) varying from 7 to 21 $h^{-1}$.

Analysis of the products is performed by using an on-line gas chromatography.

Example 1

According to the Invention

The catalyst used here is a crystalline silicate of the FER structure. The H-FER has a Si/Al of 33 under powder form. The catalyst is calcinated with air at 550° C. during 4 hours before formulation in pellets of 35-45 mesh, An isobutanol/water mixture having the 95/5 wt % composition has been processed on the catalyst under 2 bara, at temperatures between 350 and 375° C., and with an isobutanol space velocity from 7 to 21 $h^{-1}$.

In this set of operating conditions, isobutanol conversion is almost complete, with a butenes selectivity of over 95% wt, and an iso-butene selectivity of around 41-43%. Low amounts of $C_4^+$ compounds are formed.

| FEED | iButOH/H2O (95/5)% wt | | | | |
|---|---|---|---|---|---|
| P (bara) | 2 | 2 | 2 | 2 | 2 |
| T (° C.) | 350.0 | 350.0 | 350.0 | 375.0 | 375.0 |
| WHSV (H-1) | 7.3 | 12.6 | 21.0 | 21.0 | 12.6 |
| conversion (% wt CH2) | 100.0 | 99.4 | 89.7 | 99.8 | 99.2 |
| Oxygenates on C-basis (% wt CH2) - average | | | | | |
| Ether | 0.0 | 0.0 | 0.0 | 0.0 | 0.0 |
| Other alcohol | 0.1 | 0.1 | 0.2 | 0.1 | 0.1 |
| Aldehyde + Ketone | 0.1 | 0.1 | 0.1 | 0.1 | 0.1 |
| Yield on C-basis (% wt CH2) - average | | | | | |
| Paraffins | 1.0 | 0.4 | 0.2 | 0.4 | 0.4 |
| C2= | 0.8 | 0.5 | 0.3 | 0.7 | 0.4 |
| C3= | 0.2 | 0.1 | 0.0 | 0.1 | 0.1 |
| C4= | 95.9 | 97.4 | 88.7 | 97.8 | 97.5 |
| C5+ olef | 1.4 | 0.6 | 0.3 | 0.5 | 0.5 |
| Dienes | 0.4 | 0.2 | 0.0 | 0.1 | 0.1 |
| Aromatics | 0.1 | 0.0 | 0.0 | 0.0 | 0.0 |
| Unknown | 0.1 | 0.0 | 0.0 | 0.0 | 0.0 |
| Selectivity on C-basis (% wt CH2) - average | | | | | |
| Paraffins | 1.0 | 0.4 | 0.2 | 0.4 | 0.4 |
| C2= | 0.8 | 0.5 | 0.3 | 0.7 | 0.4 |
| C3= | 0.2 | 0.1 | 0.0 | 0.1 | 0.1 |
| C4= | 95.9 | 98.0 | 98.8 | 97.9 | 98.3 |
| C5+ olef | 1.4 | 0.6 | 0.3 | 0.5 | 0.5 |
| Dienes | 0.4 | 0.2 | 0.0 | 0.1 | 0.1 |
| Aromatics | 0.1 | 0.0 | 0.0 | 0.0 | 0.0 |
| Unknown | 0.1 | 0.0 | 0.0 | 0.0 | 0.0 |
| C4= distribution (% wt CH2) | | | | | |
| i-C4= | 43.4 | 42.2 | 42.4 | 42.2 | 41.6 |
| n-C4= | 56.6 | 57.8 | 57.6 | 57.8 | 58.4 |
| t-2-C4= | 27.0 | 27.7 | 27.9 | 27.0 | 28.0 |
| c-2-C4- | 18.4 | 18.7 | 18.6 | 18.7 | 18.9 |
| 1-C4= | 11.2 | 11.4 | 11.1 | 12.1 | 11.5 |

Comparative Example 2

The catalyst is cylinder-shaped gamma-alumina from Sasol® formulated. The catalyst has a specific surface are of 182 $m^2/g$ and a porous volume of 0.481 ml/g. The impurities present on the alumina in small amount are summarized below:

0.25% wt Si, 0.02% wt P, 0.02% wt fe, 29 ppm Na.

An isobutanol/water mixture having the 95/5 wt % composition has been processed on the catalyst under 2 bara, at temperatures between 350 and 380° C., and with an isobutanol space velocity from 7 to 12 $h^{-1}$.

In this set of operating conditions, isobutanol conversion is almost complete, with a butenes selectivity of over 98% wt, and an iso-butene selectivity of around 90-94%. Thus very low amounts of n-butenes are produced over this catalyst. Low amounts of $C_5^+$ compounds are formed.

| FEED | i-ButOH/H2O (95/5)% wt | | | |
|---|---|---|---|---|
| P (bara) | 2 | 2 | 2 | 2 |
| T (° C.) | 380.0 | 350.0 | 350.0 | 325.0 |
| WHSV (H-1) | 12.4 | 7.4 | 12.4 | 7.4 |
| Conversion (% wt CH2) | 99.98 | 99.96 | 99.93 | 99.85 |
| Oxygenates (% wt CH2) - average | | | | |
| Other Oxygenates | 0.0 | 0.0 | 0.0 | 0.0 |
| Other alcohol | 0.0 | 0.1 | 0.1 | 0.1 |
| Selectivity on C-basis (% wt CH2) - average | | | | |
| Paraffins | 0.3 | 0.3 | 0.1 | 0.3 |
| C2= | 0.3 | 0.2 | 0.2 | 0.1 |
| C3= | 0.2 | 0.1 | 0.0 | 0.0 |
| C4= | 98.2 | 98.6 | 99.1 | 98.6 |
| C5+ olef | 0.7 | 0.5 | 0.1 | 0.3 |
| Dienes | 0.1 | 0.0 | 0.0 | 0.1 |
| Aromatics | 0.0 | 0.0 | 0.0 | 0.0 |
| Unknown | 0.1 | 0.1 | 0.3 | 0.4 |
| C4= distribution (% wt) | | | | |
| iC4= | 90.2 | 92.5 | 92.7 | 94.0 |
| t-2-C4= | 3.0 | 1.8 | 1.4 | 1.2 |
| c-2-C4- | 3.9 | 3.2 | 3.3 | 2.7 |
| 1-C4= | 2.9 | 2.5 | 2.6 | 2.1 |
| n-C4= | 9.8 | 7.5 | 7.3 | 6.0 |

Example 3

According to the Invention

The catalyst is a phosphorous modified zeolite (P-ZSM5), prepared according to the following recipe. A sample of zeolite ZSM-5 (Si/Al=13) in H-form was steamed at 550° C. for 6 h in 100% $H_2O$. The steamed solid was subjected to a contact with an aqueous solution of $H_3PO_4$ (85% wt) for 2 h under reflux condition (4 ml/1 g zeolite). Then 69.9 g of $CaCO3$ was introduced by maintaining a pH of 2.52. Then the solution was dried by evaporation for 3 days at 80° C. 750 g of the dried sample was extruded with 401.5 g of Bindzil and 0.01 wt % of extrusion additives. The extruded solid was dried at 110° C. for 16 h and calcinated at 600° C. for 10 h.

An isobutanol/water mixture having the 95/5 wt % composition has been processed on the catalyst under 1.5 bara, at temperatures between 280 and 350° C., and with an isobutanol space velocity of about 7 $h^{-1}$.

In this set of operating conditions, isobutanol conversion is almost complete, with a butenes selectivity of over 90% wt, and an iso-butene selectivity of about 66-67%. Thus, nearly 90% or more butenes are produced of which a significant amount are skeletal isomerised into n-butenes. The heavies production is limited to 10% or less.

| FEED: i-ButOH/H2O (95/5)% wt | | |
|---|---|---|
| P (bara) | 1.5 | 1.5 |
| T (° C.) | 300 | 280 |
| WHSV (H-1) | 7.4 | 7.4 |
| Conversion (% wt CH2) | 100.0 | 83.5 |
| Oxygenates (% wt CH2) - Average | | |
| Other alcohols | 0.01 | 0.00 |
| Other Oxygenates | 0.03 | 0.08 |
| Selectivity on C-basis (% wt CH2) - Average | | |
| Paraffins C1-C4 | 0.1 | 0.1 |
| C2= | 0.0 | 0.0 |
| C3= | 0.5 | 0.3 |
| C4= | 89.9 | 93.9 |
| i-Butene | 60.3 | 61.9 |
| 1-Butene | 5.0 | 6.1 |
| 2-Butene | 24.6 | 26.0 |
| C5+ olef | 4.8 | 2.7 |
| C5+ paraf | 1.9 | 1.1 |
| Dienes | 0.5 | 0.4 |
| Aromatics | 0.5 | 0.2 |
| Unknown | 1.6 | 1.1 |
| C4= distribution - Average | | |
| i-Butene | 67.1 | 65.9 |
| n-butenes | 32.9 | 34.1 |
| 1-Butene | 5.5 | 6.5 |
| 2-Butene | 27.4 | 27.7 |

What is claimed:

1. A process for the simultaneous dehydration and skeletal isomerisation of isobutanol to make substantially corresponding olefins, having the same number of carbons and including a mixture of n-butenes and iso-butene, said process comprising:
   a) introducing in a reactor a stream (A) comprising isobutanol, optionally water, and optionally an inert component, wherein the isobutanol is present in the stream (A) in an amount ranging from 30 to 100 weight percent based on a total weight of the stream (A),
   b) contacting said stream (A) with a catalyst in said reactor at conditions effective to dehydrate and skeletal isomerase the iso-butyl moiety of at least a portion of the isobutanol to make a mixture of n-butenes and iso-butene,
   c) recovering from said reactor a stream (B), removing water, the inert component if any and unconverted isobutanol if any to get a mixture of n-butenes and iso-butene,
   wherein the WHSV of the isobutanol is at least 1 h$^{-1}$ and the catalyst is capable of simultaneously catalyzing the dehydration of the isobutanol and skeletal isomerization of butene; and
   wherein the catalyst is:
      a crystalline silicate of the group FER, MWW, EUO, MFS, ZSM-48, MTT, MFI, MEL or TON having Si/Al higher than 10,
      or a dealuminated crystalline silicate of the group FER, MWW, EUO, MFS, ZSM-48, MTT, MFI, MEL or TON having Si/Al higher than 10,
      or a phosphorus modified crystalline silicate of the group FER, MWW, EUO, MFS, ZSM-48, MTT, MFI, MEL or TON having Si/Al higher than 10,
      or a silicoaluminaphosphate molecular sieve of the group AEL,
      or a silicated, zirconated or titanated or fluorinated alumina.

2. The process according to claim 1 wherein the WHSV of the isobutanol is from 1 to 30 h$^{-1}$.

3. The process according to claim 2 wherein the WHSV of the isobutanol is from 2 to 21 h$^{-1}$.

4. A process for the simultaneous dehydration and skeletal isomerisation of isobutanol to make substantially corresponding olefins, having the same number of carbons and including a mixture of n-butenes and iso-butene, said process comprising:
   a) introducing in a reactor a stream (A) comprising isobutanol, optionally water, and optionally an inert component, wherein the isobutanol is present in the stream (A) in an amount ranging from 30 to 100 weight percent based on a total weight of the stream (A),
   b) contacting said stream (A) with a catalyst in said reactor at conditions effective to dehydrate and skeletal isomerise the iso-butyl moiety of at least a portion of the isobutanol to make a mixture of n-butenes and iso-butene,
   c) recovering from said reactor a stream (B), removing water, the inert component if any and unconverted isobutanol if any to get a mixture of n-butenes and iso-butene,
   wherein the temperature in the reactor ranges from 200° C. to 600° C. and the catalyst is capable of simultaneously catalyzing the dehydration the isobutanol and skeletal isomerization of butene; and
   wherein the catalyst is:
      a crystalline silicate of the group FER, MWW, EUO, MFS, ZSM-48, MTT, MFI, MEL or TON having Si/Al higher than 10,
      or a dealuminated crystalline silicate of the group FER, MWW, EUO, MFS, ZSM-48, MTT, MFI, MEL or TON having Si/Al higher than 10,
      or a phosphorus modified crystalline silicate of the group FER, MWW, EUO, MFS, ZSM-48, MTT, MFI, MEL or TON having Si/Al higher than 10,
      or a silicoaluminaphosphate molecular sieve of the group AEL,
      or a silicated, zirconated or titanated or fluorinated alumina.

5. The process according to claim 4 wherein the pressure of the reactor ranges from 0.5 to 10 bars absolute.

6. The process according to claim 4 wherein the temperature ranges from 250° C. to 500° C.

7. The process according to claim 6 wherein the temperature ranges from 300° C. to 450° C.

8. The process according to claim 4 wherein the stream (B) is fractionated in a step d) to produce an n-butenes stream (N) and to remove isobutene optionally recycled with stream (A) to the reactor of step b).

9. The process according to claim 8 wherein in the fractionation of step d) iso-butene is removed by selective oligomerisation of iso-butene.

10. The process according to claim 8 wherein in the fractionation of step d) iso-butene is removed by selective etherification with methanol or ethanol.

11. The process according to claim 8 wherein in the fractionation of step d) iso-butene is removed by selective hydration into t-butanol.

12. The process according to claim 11 wherein said t-butanol is recycled to the reactor at step b).

13. The process according to claim 8 wherein the fractionation of step d) is made by a catalytic distillation column wherein 1-butene is isomerised to 2-butene, iso-butene is recovered as overhead and 2-butene is recovered in a bottoms of said catalytic distillation column.

14. The process according to claim 13 wherein iso-butene is recycled to the reactor at step b).

15. The process according to claim 14 wherein among the butenes produced at step c) the proportion of n-butenes is above 20%.

16. The process according to claim 15 wherein among the butenes produced at step c) the proportion of n-butenes is above 30%.

17. The process according to claim 16 wherein among the butenes produced at step c) the proportion of n-butenes is above 40%.

18. The process according to claim 17 wherein among the butenes produced at step c) the proportion of n-butenes is above 50%.

19. The process according to claim 1, wherein the catalyst is the silicoaluminaphosphate molecular sieve of the group AEL.

20. The process according to claim 1, wherein the catalyst is the silicated, zirconated or titanated or fluorinated alumina.

21. The process according to claim 1, wherein the catalyst is the crystalline silicate of the group FER, MWW, EUO, MFS, ZSM-48, MTT, MFI, MEL or TON having Si/Al higher than 10.

22. The process according to claim 1, wherein the catalyst is the dealuminated crystalline silicate of the group FER, MWW, EUO, MFS, ZSM-48, MTT, MFI, MEL or TON having Si/Al higher than 10.

23. The process according to claim 1, wherein the catalyst is the phosphorus modified crystalline silicate of the group FER, MWW, EUO, MFS, ZSM-48, MTT, MFI, MEL or TON having Si/Al higher than 10.

24. The process according to claim 1, wherein the catalyst is a crystalline silicate of the group FER or MFI having Si/Al higher than 10, a dealuminated crystalline silicate of the group FER or MFI having Si/Al higher than 10, or a phosphorus modified crystalline silicate of the group FER or MFI having Si/Al higher than 10.

25. The process according to claim 1, wherein the mixture of n-butenes and iso-butene contains from 35 to 50 weight percent iso-butene.

26. The process according to claim 1, a ratio of isobutanol to all other $C_4$ alcohols in the stream (A) is 42% or above.

27. The process according to claim 1, a ratio of isobutanol to all other $C_4$ alcohols in the stream (A) is 70% or above.

28. The process according to claim 1, a ratio of isobutanol to all other $C_4$ alcohols in the stream (A) is 80% or above.

* * * * *